United States Patent [19]

Bull

[11] Patent Number: 5,310,549
[45] Date of Patent: May 10, 1994

[54] SOLID CONCENTRATE IODINE COMPOSITION

[75] Inventor: Sandra L. Bull, Eagan, Minn.

[73] Assignee: Ecolab Inc., St. Paul, Minn.

[21] Appl. No.: 401,092

[22] Filed: Aug. 31, 1989

[51] Int. Cl.[5] ............................................. A01N 59/22
[52] U.S. Cl. ................... 424/78.08; 424/667; 424/668; 424/669
[58] Field of Search ................. 424/667, 668, 669, 78, 424/81, 78.08

[56] References Cited

U.S. PATENT DOCUMENTS

| | | | |
|---|---|---|---|
| 2,739,922 | 3/1956 | Shelanski | 424/668 |
| 2,759,869 | 8/1956 | Sutton et al. | 167/70 |
| 3,029,183 | 4/1962 | Winicov et al. | 167/17 |
| 3,150,096 | 9/1964 | Schmidt et al. | 252/106 |
| 3,438,906 | 4/1969 | Duvall | 252/106 |
| 3,525,696 | 8/1970 | Schmidt et al. | 252/106 |
| 3,650,965 | 3/1972 | Cantor et al. | 252/106 |
| 4,017,407 | 4/1977 | Cantor et al. | 424/80 |
| 4,077,898 | 3/1978 | Rue | 252/106 |
| 4,624,713 | 11/1986 | Morganson et al. | 134/25 |
| 4,690,305 | 9/1987 | Copeland | 222/52 |
| 4,801,460 | 6/1989 | Goertz et al. | 424/80 |
| 5,019,346 | 5/1991 | Richter et al. | 422/264 |

OTHER PUBLICATIONS

Chem. Abstracts 106: 182671b.
Chem. Abstracts 108: 226916p.
U.S. Ser. No. 07/052,798 to Copeland (Application Pending).
U.S. Ser. No. 07/247,279 to Richter et al (Application Pending).

Primary Examiner—Thurman K. Page
Assistant Examiner—Peter Kulkosky
Attorney, Agent, or Firm—Merchant, Gould, Smith, Edell, Welter & Schmidt

[57] ABSTRACT

A solid iodine concentrate composition comprising an iodine complex, and a solidifier wherein said iodine complex comprises a complexing agent and an iodine source present in a ratio of at least 1.5:1.

36 Claims, No Drawings

SOLID CONCENTRATE IODINE COMPOSITION

FIELD OF THE INVENTION

The invention relates to germicidal iodine compositions. More specifically, the present invention relates to solid germicidal iodine concentrates which may be diluted to form a use solution for disinfecting and sanitizing purposes. Such use solutions have found application in environments including institutional health care settings, restaurant and food preparation facilities, and food manufacturing and processing plants among others.

BACKGROUND OF THE INVENTION

Iodine compositions have long been known to impart desirable antimicrobial characteristics. For example, Sutton et al, U.S. Pat. No. 2,759,869, Winicov et al, U.S. Pat. No. 3,029,183, Cantor et al, U.S. Pat. No. 3,650,965 as well as Schmidt et al, U.S. Pat. Nos. 3,525,696 and 3,150,096 all disclose aqueous liquid or said iodine use dilution compositions for various uses.

Iodine compositions have been found preferable for any number of uses due to the high antimicrobial efficacy and nonstaining character of complexed iodine compositions. Iodine compositions are known to be useful as sanitizers for elements ranging from contact surfaces and glassware to plant formulation facilities. An especially important application for iodine compositions is in clean-in-place (CIP) systems. CIP systems are generally found in industries which produce fluidized ingestible products for humans or animals such as the dairy industry, the pharmaceutical industry, and the food industry. Clean-in-place systems are generally regarded as large production plant systems having reservoirs, pipes, pumps and mixing vessels which cannot be broken down to be cleaned. Additionally, clean-in-place preparation systems often require high sanitization when used in the production of ingestible substances.

Previously iodine compositions were either formulated as liquids or as free flowing powders. In either case these compositions require stabilizing systems which are most often present at a concentration many times that of the iodine in the system. Moreover, these iodine compositions do not economize on volume or weight in that they obtain stabilization of iodine generally only at use-dilution concentrations Such a high concentration of stabilizer can result in excess foaming which may cause inactivation of pump systems, foaming on application surfaces, and prevent rapid draining in warewashing operations. Thus, the high concentration of stabilizer may prevent the effective cleaning of pumps and pipelines. Also, stabilizer systems are often costly, and, as a result, may raise the expense of the clean-in-place composition to a premium which often cannot be justified for a composition which will be used once and then discarded.

Accordingly, there is a need for a solid iodine composition which contains a concentrated volume of iodine in proportion to the concentration of stabilizing agent thereby providing a system with reduced foaming and potentially increased sanitizing efficacy.

SUMMARY OF THE INVENTION

We have found a solid iodine concentrate composition comprising an iodine complex which comprises an iodine source and a complexing agent, a solidifier, and optionally an acidulant. The complexing agent and the iodine source may be present at a ratio as low as about 1.5:1. The concentrate composition may be diluted to create use solution having an active iodine concentration of at least 12.5 ppm.

In accordance with a further aspect of the present invention there is provided a method of using a solid iodine concentrate composition comprising an iodine source, complexing agent, a solidifier, and optionally an acidulant, comprising the step of dissolving said concentrate composition to use dilutions to form an antimicrobial solution.

The concentrate composition of the present invention provides a use solution having variable levels of foaming depending upon the iodine/complexing agent ratio and the complexing agent used. In greater detail, one embodiment of the present invention provides an iodine use solution having minimum foaming preferable for clean-in-place systems. In that the composition of the present invention is a solid concentrate, there are additional advantages provided through the use of this composition. Specifically, the solid concentrate composition of the present invention provides the user with added safety and convenience by reducing the potential for spillage and any resulting direct skin contact between the user and the composition. Additionally, the concentrated nature of the present composition reduces the volume of the product needed for any given application as well as economizing on transportation costs, storage space, and raw materials.

DETAILED DESCRIPTION OF THE PREFERRED EMBODIMENT

The composition of the present invention is a solid concentrate iodine composition generally comprising an iodine complex which includes an iodine source as well as a complexing agent, a hardener, and optionally an acidulant, defoaming agent.

IODINE COMPLEX

A principle constituent of the present invention is the iodine complex which generally comprises an iodine source and a complexing agent. Turning first to iodine, the function of the iodine source is to provide disinfecting or sanitizing antimicrobial efficacy as equated with the definitions provided by the Association of Analytical Chemists Official Methods of Analysis §§4.020 to 4.029 for determining disinfecting and sanitizing antimicrobial efficacy. Iodine is generally chosen over other elemental sanitizing agents due to its high antimicrobial efficacy over short periods of time.

Iodine is a nonmetallic element belonging to the halogen family in Group VIIA of the periodic table. It is the heaviest common member of this family and the only one that is solid at ambient temperatures. Iodine, like the other halogens, is very active chemically, but more desirable than other halogens as being less violent in its action. Iodine is slightly soluble in water, the solubility increasing with temperature. Iodine also dissolves in many organic solvents.

While iodine may be used in its elemental form, generally, iodine as used in the present invention is a premix composition which generally comprises iodine, an iodide constituent such as sodium iodide, potassium iodide or hydroiodic acid, and water. Generally, the iodine in the present composition is present at a concentration ranging from about 0.5 wt % to 10 wt-%, preferably 2 wt-% to 8 wt-%, and most preferably 3 wt-% to 6 wt-%.

One principle advantage of the present composition is the ability to provide an extremely high concentration of iodine within the concentrate with an unexpectantly low concentration of complexing agent used to stabilize the iodine. Generally, the ratio of complexing agent to iodine at least about 1.5:1, preferably from about 1.7:1 to about 3:1, and most preferably from about 1.8:1 to about 2.3:1.

Increasing the concentration of iodine within the composition will increase the ratio at which the product may be diluted. Moreover, increasing the concentration of iodine within the composition may generally increase physical softness of the product and in turn increase the rate of dissolution. The relative physical hardness of the composition will be dependent upon the ratio of complexing agent to iodine as well as the concentration of the solidifying agent. In contrast, decreasing the concentration of iodine in the concentrate composition of the present invention will decrease the dilution rate while coincidently increasing the hardness of the product.

The iodine complex also comprises a complexing agent which generally functions to releasably hold the iodine in the solid concentrate form within a network or matrix formed with the urea. Generally, iodine may be complexed to prevent sublimation, prevent staining by the iodine constituent upon application surfaces, and to solubilize the iodine once diluted with an aqueous or organic solvent. Accordingly, once placed in solution, the complexing agent additionally functions to solubilize the iodine in the dilute aqueous system. This prevents the iodine from separating creating two phases or settling out of the diluent solution.

Generally, the complexing agent may comprise any composition which will releasably hold iodine within the solid concentrate composition of the present invention. Moreover, the complexing agent should comprise a constituent or constituents which facilitates dispersion and solubilization of the iodine once the concentrate is diluted into a liquid system. Generally, the complexing agent may be any number of different polymers or compounds which are useful in tying up the iodine constituent and then controllably releasing the iodine constituent over time. For example, the complexing agent may comprise a surface active agent such as a nonionic, anionic or cationic surfactant, polyvinyl pyrrolidones, phosphate esters of ethoxylated alcohols or any number of other known complexing agents which will allow the formation of a solid concentrate iodine composition having an iodine to complexing agent ratio of more than 1:1.5.

Along these lines surfactants, and especially nonionic surfactants, have been found to be especially useful in complexing the iodine composition of the present invention. Nonionic surfactants which have generally been found to be useful in the present invention are those which comprise ethylene oxide moieties, propylene oxide moieties, as well as mixtures thereof, and ethylene oxide-propylene oxide moieties in either heteric or block formation. Additionally useful in the present invention are nonionic surfactants which comprise an alkyl ethylene oxide compounds, alkyl propylene oxide compounds, as well as mixtures thereof, and alkyl ethylene oxide-propylene oxide compounds where the ethylene oxide propylene oxide moiety is either in heteric or block formation. Further useful in the present invention are nonionic surfactants having any mixture or combination of ethylene oxide-propylene oxide moieties linked to a alkyl chain where the ethylene oxide and propylene oxide moieties may be in any randomized or ordered pattern and of any specific length. Nonionic surfactants useful in the present invention may also comprise randomized sections of block and heteric ethylene oxide propylene oxide, or ethylene oxide-propylene oxide.

Two specific types of nonionic surfactants have been found to be preferable as complexing agents in the solid concentrate composition of the present invention. First, polyoxypropylene-polyoxyethylene block polymers having a molecular weight of at least 1900 have been found to be especially useful in the present invention. These polymers generally have the formula:

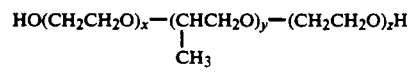

in which on the average x=0–150, preferably, 2–128, y=0–150, and preferably, 16–70, and z=0–150, and preferably, 2–128.

More preferably, the polyoxypropylene-polyoxyethylene copolymers used in the present invention have a x=2–40, a y=30–70 and a z=2–40. Block nonionic copolymers of this formula are desirable for clean-in-place application due to the reduced foaming characteristics these provide.

A second class of nonionic surfactants which is useful in the present invention and desirable for other applications are alcohol ethoxylates. Such nonionics are formed by reacting an alcoholate salt ($RO^-Na^+$) wherein R is an alcohol or alkyl aromatic moiety with an alkylene oxide. Generally, preferred alkoxylates are $C_{1-12}$ alkyl phenol alkoxylates such as the nonyl phenol ethoxylate which generally have the formula:

where n may range in value from 6 to 100.

Nonyl phenol ethoxylates having an ethoxylate molar value ranging from about 6 moles to 15 moles have been found preferable for reasons of low foaming character and complexing stability provided to the composition of the present invention.

Generally, the concentration of complexing agent used in the present invention may range from about 5% to about 25% of the concentrate composition, preferably from about 5% to about 20% of the concentrate composition, and most preferably from about 5% to about 15% of the concentrate composition. Varying the concentration of complexing agent alters the chemical and physical characteristics of the solid composition of the present invention as well as the use dilution iodine solution resulting from the solid concentrate. Specifically, increasing the level of complexing agent may be used to limit the concentration of iodine released into any given system.

In sharp contrast, decreasing the level of complexing agent will result in a concentrate composition having a softer character where the iodine may be more readily released from the system. Also, decreasing the level of complexing agent will effect the stability of the iodine once the solid concentrate is dissolved in the use solution. Too great a decrease in complexing agent may result in a phase separation or settling out of the iodine.

THE SOLIDIFYING AGENT

The solidifying agent functions to solidify the concentrate composition and stabilize the iodine in a solid form. Generally, anything which will solidify the iodine complex while not detracting from the eventual release of the iodine into the use solution may be used as a solidifying agent in the present invention. While it may be possible to use other solidifying compositions in the present invention, urea, $NH_2CONH_2$, has been found to be especially useful in the composition of the present invention as a solidifying agent.

Generally, the concentration of urea within the solid concentrate composition of the present invention ranges from about 30% to 70%, preferably about 40% to 60%, and most preferably about 40% to 50%. Here again, varying the concentration of the urea solidifier within the present composition will vary the physical chemical characteristics of the composition. Accordingly, increasing the concentration of the urea hardener in the present composition will generally tend to increase the hardness of the solid composition. In sharp contrast, decreasing the concentration of solidifying agent will tend to loosen or soften the concentrate composition.

ACIDULANT

The solid iodine concentrate composition of the present invention may also contain an acidulant or acid source. The acidulant functions to reduce the pH of the composition and, in turn, increase the antimicrobial efficacy of the iodine constituent by shortening the kill time of the composition. Also, to the extent that it is present, the acidulant functions to facilitate removal of salt buildup in pipelines and other application surfaces exposed to the composition.

Generally, any acid source which will not interfere with the formation of a solid product, or the activity of the iodine when subsequently diluted may be used in the composition of the present invention. Both organic and inorganic acids have been found to be generally useful in the present composition. Especially useful in the present composition are acids such as phosphoric acid, citric acid, and sulfamic acid. Also useful in the present invention are certain inorganic salts which will buffer the system at an acidic pH such as sodium bisulfate.

Generally, the concentration of acidulant within the concentrate composition of the present invention ranges from about 5% to 50%, preferably about 20% to 50% and most preferably 30% to about 40%. Here again, varying the concentration of acidulant within the concentrate composition of the present invention will alter the chemical characteristics of the resulting composition.

Specifically, reducing the concentration of acidulant may increase the pH of the use solution and may ultimately result in raising the kill time for the specific compositions once applied. In sharp contrast, increasing the concentration of acidulant within the composition of the present invention will decrease the pH of the use solution and in turn, decrease the amount of time it takes to kill off the bacteria present in the system. However, increasing the concentration of acidulant past a certain point will no longer provide measurable decreases in the length of time needed to kill off ambient bacteria and, additionally, may create a system which is corrosive to tanks and pipes.

The concentrate iodine composition of the present invention may also contain additional ingredients as necessary to assist in defoaming. Generally, defoamers which have been found useful in the present invention include fatty acids such as coconut fatty acid; fatty alcohols; and phosphate esters. These defoamers are generally present at a concentration range from about 0 wt-% to 1.0 wt-%, preferably from about 0.05 wt-% to 0.5 wt-%, and most preferably from about 0.10 wt-% to about 0.50 wt-%.

The concentrate composition of the present invention may also comprise fragrances, dyes, fillers, additional hardening agents, or additional complexing agents among other constituents which may be included to increase the aesthetic appeal of the composition, reduce the foaming, or functionally alter the concentrate composition of the present invention as desired for any intended use.

| Constituent | Concentration Range | | |
|---|---|---|---|
| | Useful | Working | Preferred |
| Iodine | 0.5–10 wt-% | 2–8 wt-% | 3–6 wt-% |
| Complexing Agent | 5–25 wt-% | 5–20 wt-% | 5–15 wt-% |
| Solidifier | 30–70 wt-% | 40–60 wt-% | 40–60 wt-% |
| Acidulant | 0–50 wt-% | 20–50 wt-% | 30–40 wt-% |
| Defoamer | 0–1 wt-% | 0.05–0.5 wt-% | 0.1–0.5 wt-% |

FORMULATION AND USE

Generally, the concentrate composition of the present invention is formulated by first charging the acidulant into a mixing vessel and heating. The hardening agent, generally urea is then charged into the vessel with continued heating until melted. Mixing is continued while the complexing agent and any defoamers which are needed in the composition are added. The mixture is then cooled to a temperature of about 120° to 130° F. The iodine source is then added to the composition slowly with concerted mixing to prevent more separation and to ensure uniformity. The formulation is then further mixed until homogenous and then allowed to cool and solidify which generally occurs below 120° F.

In application, the solid composition of the present invention is generally dissolved in and diluted with water or any other desirable diluent. Generally, any concentration of iodine may be used in the final application solution. However, we have found that an effective iodine concentration of 12.5 parts per million provides a requisite level of antimicrobial efficacy.

Generally, the concentrate composition of the present invention may take any number of forms. Specifically, the form in which the concentrate composition of the present invention takes may vary depending on the given application in which the composition is intended to be used. Different forms of the concentrate composition will be required for clean-in-place applications as opposed to warewashing applications or the use of the concentrate composition to prepare a stock solution for surface cleaning. For instance, the composition of the present invention may be housed in a tub or capsule, the capsule being of a polymeric nature such as polyethylene, polypropylene, or PVC. The solid concentrate composition may be cast into the tub or capsule on a manner so that it is either releasable from the capsule or firmly held within the capsule. The capsule may subsequently be covered with a hermetic seal such as an adhesively sealed alloy foil or polymeric film. Additionally, the tub or capsule may be sealed with a polymeric snap on lid. The size of the tub or capsule may range generally over any broad volume and weight with a preferred size being approximately 0.10 pound to 10 pounds.

In application, the sealing cover of the plastic tub or capsule will be removed to expose the iodine concentrate composition of the present invention. The concentrate composition will then be removed from the tub and inserted into any number of dispensers which may be used in the present invention. Alternatively, the concentrate including the tub may be inserted into the dispenser once the cover or sealing film has been removed. The exposed surface of the concentrate will then be contacted with the diluent which is usually aqueous, to create a liquid stock solution. The liquid stock solution may be either used in its present concentrate or further diluted with water to create a solution having a lesser concentration.

An alternative embodiment of the composition of the present invention is a pelletized form of the iodine concentrate composition. The composition of the present invention may be pelletized through methods well known to those skilled in the art. Generally, the dimensions of the pelletized concentrate composition may range from less than 0.5 inches in length, width, and height and weighing 2-5 grams to a pellet which may have a size of up to eight inches in length, width and height weighing over 1.0 kilogram. Generally, the use of such a pelletized system would comprise the application of the pellet having a known weight, into a reservoir of a known volume of diluent and dissolving the pellet within that diluent. The pelletized composition may also be inserted in a water soluble bag and used in a dispenser to provide multiple autonomous stock solutions from the concentrate composition over time.

WORKING EXAMPLES

The Working Examples provided below were formulated in two parts. The first part generally comprised an iodine premix and the second part, the formulatory examples, generally comprised the solid iodine concentrate composition in completed form.

IODINE PREMIX

The iodine premix was generally formulated by adding deionized water, iodine, and the iodide constituent to the reactor with adequate mixing. Generally, the iodide constituent can be any alkaline earth metal-iodine salt such as sodium iodide or potassium iodide or for that matter hydroiodic acid, HI.

| Constituent | wt-% |
|---|---|
| Iodine (as $I_2$) | 59.00 |
| Iodide (as NaI) | 24.00 |
| $H_2O$ | 17.00 |

THE FORMULATORY WORKING EXAMPLES

The following Formulatory Examples incorporated the iodine premix into a solid concentrate compositional form. In formulation, the complexing agent, urea, and phosphoric acid were heated to 170° F. for mixing, and then cooled to a temperature of about 130° F. at which point the iodine premix was added. This step in formulation minimized the loss of iodine premix and, in turn, reduced the loss of the iodine. After mixing the Formulatory Working Examples were then decanted at a temperature of 100° F. to 120° F. into a container. The weight percentage of phosphoric acid used in each example is defined in terms of weight of acid as a percentage of aqueous diluent.

Working Examples 1 and 2 comprised:

|  | #1 | #2 |
|---|---|---|
| Phosphoric Acid - (75% w/v) | 33.30% | |
| Phosphoric Acid - (85% w/v) | | 29.50% |
| Urea, prilled | 39.20% | 43.00% |
| Pluronic L-44 (polyoxyethylene, polyoxypropylene block polymer available from BASF - Wyandotte Corp. and having 22 moles of ethylene oxide and 21 moles of propylene oxide) | 20.80% | 20.80% |
| Emery 622 (coconut fatty acid commercially available from Emery Chemicals) | 0.20% | 0.20% |
| Iodine Premix | 6.50% | 6.50% |
|  | 100.00% | 100.00% |

Working Examples 1 and 2 were solid when cooled to room temperature.

working Example 3 was made using a lesser amount Pluronic L-44 to possibly increase the rate of thickening.

|  | #3 |
|---|---|
| Phosphoric Acid - (85% w/v) | 29.50% |
| Urea, Prilled | 48.00% |
| Pluronic L-44 (polyoxyethylene, polyoxypropylene block polymer available from BASF - Wyandotte Corp. and having 22 moles of ethylene oxide and 21 moles of propylene oxide) | 15.80% |
| Emery 622 (coconut fatty acid commercially available from Emery Chemicals) | 0.20% |
| Iodine Premix | 6.50% |
|  | 100.00% |

After formulation, Working Example 3 hardened at room temperature.

Working Example 4 was formulated using 75% (w/v) phosphoric acid and Working Example 5 was formulated using 85% (w/v) phosphoric acid. Working Examples 4 and 5 were also formulated with Pluronic P-85, which is a solid at room temperature.

|  | #4 | #5 |
|---|---|---|
| Phosphoric Acid (75% w/v) | 33.30% | |
| Phosphoric Acid (85% w/v) | | 34.50% |
| Urea | 39.97% | 48.80% |
| Pluronic P-85 (polyoxyethylene, polyoxypropylene block polymer available from BASF - Wyandotte Corp. and having generally 54 moles of ethylene oxide and 39 moles of propylene oxide) | 20.00% | 10.00% |
| Emery 622 (coconut fatty acid commercially available from Emery Chemicals) | 0.20% | 0.20% |
| Iodine Premix | 6.50% | 6.50% |

-continued

|  | #4 | #5 |
|---|---|---|
|  | 100.00% | 100.00% |

Working Example 4 thickened after addition of the Pluronic and slowly hardened at room temperature. Working Example 5 went together easily at 120°, immediately starting to thicken and hardened after one hour at room temperature.

Working Example 6 was formulated using a Pluronic P-65 nonionic surfactant to possibly increase high temperature stability.

|  | #6 |
|---|---|
| Phosphoric Acid (85% w/v) | 34.50% |
| Urea | 48.80% |
| Pluronic P-65 (polyoxyethylene, polyoxypropylene block polymer commercially available from BASF - Wyandotte generally having 38 moles of ethylene oxide and 30 moles of propylene oxide) | 10.00% |
| Emery 622 (coconut fatty acid commercially available from Emery Chemicals) | 0.20% |
| Iodine Premix | 6.50% |
|  | 100.00% |

Working Example 6 hardened at room temperature after mixing.

Working Examples 7 and 8 were formulated as 1000 gram batches using Pluronic P-104 and P-105, respectively. Both were split and one sample each was placed in 122° oven overnight.

|  | #7 | #8 |
|---|---|---|
| Phosphoric Acid (85% w/v) | 34.50% | 34.50% |
| Urea | 48.80% | 48.80% |
| Pluronic (P-104) (polyoxyethylene, polyoxypropylene block polymer commercially available from BASF - Wyandotte generally having 62 moles of ethylene oxide and 54 moles of propylene oxide) | 10.00% |  |
| Pluronic (P-105) (polyoxyethylene, polyoxypropylene block polymer commercially available from BASF - Wyandotte generally having 76 moles of ethylene oxide and 54 moles of propylene oxide) |  | 10.00% |
| Emery 622 (coconut fatty acid commercially available from Emery Chemicals) | 0.20% | 0.20% |
| Iodine Premix | 6.50% | 6.50% |
|  | 100.00% | 100.00% |

Working Example 7 became thick after the addition of Pluronic. The Emery 622 was added and the composition was mixed for about 15 minutes to ensure thorough mixing. The composition was poured at about 120° and hardened quickly.

Working Example 8 proved less thick after Pluronic addition. The Emery 622 was added before the Pluronic to insure the formation of a homogeneous mix. But when lowering the temperature to 120° in preparation for the addition of the Iodine Premix, the batch started to harden around the edges, and did not mix in well. After pouring at 120°, the product hardened quickly.

Both Working Examples 7 and 8 were placed in an elevated temperature stability overnight and afterwards both formulations maintained their form in their respective containers.

Working Example 9 was formulated with 5% P-85 and 5% P-105.

|  | #9 |
|---|---|
| Phosphoric Acid (85% w/v) | 34.50% |
| Urea | 48.80 |
| Pluronic P-85 (polyoxyethylene, polyoxypropylene block polymer available from BASF - Wyandotte Corp. and having generally 54 moles of ethylene oxide and 39 moles of propylene oxide) | 5.00% |
| Pluronic P-105 (polyoxyethylene, polyoxypropylene block polymer commercially available from BASF - Wyandotte generally having 76 moles of ethylene oxide and 54 moles of propylene oxide) | 5.00% |
| Emery 622 (coconut fatty acid commercially available from Emery Chemicals) | 0.20% |
| Iodine Premix | 6.50% |
|  | 100.00% |

FOAM PROFILE TEST

A comparative foam profile test was then conducted to determine the relative foam height of Example 7, 8, and 9 as previously formulated. First, concentrate from the three examples was diluted to a concentration of 25 ppm titratable $I_2$ (0.0006 w/v concentrate) in an aqueous solution. Then, a 150 ml of the solution to be tested was placed in a 500 ml glass cylinder having a height of 25 cm and a diameter of 6 cm. A tube with a fritted glass end injecting a constant air flow of 2 liters per minute was then placed in the solution. The foam height was recorded in millimeters with a maximum level being 400 mm. The test was run for five minutes unless 400 ml of foam was reached before this time.

TABLE I

| Sample | Foam Height |
|---|---|
| Example #7 | 400 ml in 15 seconds |
| Example #8 | 70 ml |
| Example #9 | 400 ml in 13 seconds |

As can be seen, formulatory example 8 provided the least foam of the three examples.

WORKING EXAMPLES 10 THROUGH 21

Working Examples 10–21 were formulated by adding phosphoric acid to urea and then mixing under heat to a temperature of about 170° F. The nonionic surfactant pluronic P-105 was then added in combination with the Emery 622 fatty acid and mixed thoroughly over a period of about 15 minutes. The sample was then cooled to approximately 120° F. to 130° F. after which time the iodine premix was added slowly. The composition was then decanted into 250 gm containers and placed in a water bath for cooling and solidification.

Of these Examples, Working Examples 10, 13, 20 and 21 were formulated in 1,000 gram. batches and split between room temperature and elevated temperature stability at 120° F. for 2 and 4 weeks, the elevated temperature stability samples designated 10A, 13A, 20A and 21A. The other half of Working Examples 10, 13, 20 and 21 were used for room temperature stability. The remaining Working Examples were used merely as formulatory examples.

The results of the iodine stabilities are provided in Tables I and II. Working Examples #10, 10A, 13, 20A and 21 were resampled to provide a second value for average I$_2$. Accordingly, these Examples have two entries in Tables I and II for the initial data point.

| | #10 Wt-% | #11 Wt-% |
|---|---|---|
| Phosphoric Acid (85% w/v) | 34.5 | 35.5 |
| Urea | 47.8 | 47.8 |
| Pluronic P-105 (polyoxyethylene, polyoxypropylene block polymer commercially available from BASF - Wyandotte generally having 76 moles of ethylene oxide and 54 moles of propylene oxide) | 10.0 | 10.0 |
| Emery 622 (coconut fatty acid commercially available from Emery Chemicals) | 0.2 | 0.2 |
| Iodine Premix | 7.5 | 6.5 |
| | 100.0 | 100.0 |

| | #12 Wt-% | #13 Wt-% |
|---|---|---|
| Phosphoric Acid (85% w/v) | 33.5 | 34.5 |
| Urea | 47.8 | 47.8 |
| Pluronic P-105 (polyoxyethylene, polyoxypropylene block polymer commercially available from BASF - Wyandotte generally having 76 moles of ethylene oxide and 54 moles of propylene oxide) | 10.0 | 10.0 |
| Emery 622 (coconut fatty acid commercially available from Emery Chemicals) | 0.2 | 0.2 |
| Iodine Premix | 8.5 | 7.5 |
| | 100.0 | 100.0 |

| | #14 Wt-% | #15 Wt-% |
|---|---|---|
| Phosphoric Acid (85% w/v | 39.5 | 29.5 |
| Urea | 47.8 | 47.8 |
| Pluronic P-105 (polyoxyethylene, polyoxypropylene block polymer commercially available from BASF - Wyandotte generally having 76 moles of ethylene oxide and 54 moles of propylene oxide} | 5.0 | 15.0 |
| Emery 622 (coconut fatty acid commercially available from Emery Chemicals) | 0.2 | 0.2 |
| Iodine Premix | 7.5 | 7.5 |
| | 100.0 | 100.0 |

| | #16 Wt-% | #17 Wt-% |
|---|---|---|
| Phosphoric Acid (85% w/v) | 30.5 | 40.5 |
| Urea | 47.8 | 47.8 |
| Pluronic P-105 (polyoxyethylene, polyoxypropylene block polymer commercially available from BASF - Wyandotte generally having 76 moles of ethylene oxide and 54 moles of propylene oxide) | 15.0 | 5.0 |
| Emery 622 (coconut fatty acid commercially available from Emery Chemicals) | 0.2 | 0.2 |
| Iodine Premix | 6.5 | 6.5 |
| | 100.0 | 100.0 |

| | #18 Wt-% | #19 Wt-% |
|---|---|---|
| Phosphoric Acid (85% w/v) | 38.5 | 28.5 |
| Urea | 47.8 | 47.8 |
| Pluronic P-105 (polyoxyethylene, polyoxypropylene block polymer commercially available from BASF - Wyandotte generally having 76 moles of ethylene oxide and 54 moles of propylene oxide) | 5.0 | 15.0 |
| Emery 622 (coconut fatty acid commercially available from Emery Chemicals) | 0.2 | 0.2 |
| Iodine Premix | 8.5 | 8.5 |
| | 100.0 | 100.0 |

| | #20 Wt-% | #21 Wt-% |
|---|---|---|
| Phosphoric Acid (85% w/v) | 34.5 | 34.5 |
| Urea | 47.8 | 47.8 |
| Pluronic P-105 (polyoxyethylene, polyoxypropylene block polymer commercial.y available from BASF - Wyandotte generally having 76 moles of ethylene oxide and 54 moles of propylene oxide) | 10.0 | 10.0 |
| Emery 622 (coconut fatty acid commercially available from Emery Chemicals) | 0.2 | 0.2 |
| Iodine Premix | 7.5 | 7.5 |
| | 100.0 | 100.0 |

Working Examples 14, 17, and 18 were eliminated due to problems in formulation.

TABLE I

| Elevated Temperature (122° F.) I$_2$ Stability (in % I$_2$) | | |
|---|---|---|
| Working Example | Initial | 4 Week |
| 10A | 4.634%/4.50% | 4.86% |
| 13A | 4.920% | 5.78% |
| 20A | 4.09%/4.09% | 6.22% |
| 21A | 4.22% | 5.75% |

TABLE II

| Room Temperature I$_2$ Stability (in % I$_2$) | | |
|---|---|---|
| Working Example | Initial | 4 Week |
| 10 | 4.12%/4.44% | 4.70% |
| 13 | 4.85%/4.22% | 4.47% |
| 20 | 4.280% | 4.65% |
| 21 | 4.15%/4.54% | 4.55% |

The following formulatory examples also incorporate the iodine premix into a solid concentrate compositional form. In formulation, the complexing agent, urea, and phosphoric acid are heated to 170° F. for mixing. The formulation is then cooled to a temperature of about 130° F. at which point the iodine premix is added. The formulatory working examples are then decanted at a temperature of 100° F. to 120° F. into a container. The weight percentages of phosphoric acid used in each example is defined in terms of weight of acid as a percentage of aqueous diluent.

| | #22 | #23 |
|---|---|---|
| Phosphoric Acid (75% w/v) | 33.30% | |
| Phosphoric Acid (85% w/v) | | 34.50% |
| Urea | 39.97% | 48.80% |
| Polyvinyl Pyrrolidone | 20.00% | 10.00% |
| Emery 622 (coconut fatty acid commercially available from Emery Chemicals) | 0.20% | 0.20% |
| Iodine Premix | 6.50% | 6.50% |
| | 100.00% | 100.00% |

| | #24 | #25 |
|---|---|---|
| Phosphoric Acid (75% w/v) | 33.30% | |
| Phosphoric Acid (85% w/v) | | 34.50% |
| Urea | 39.97% | 48.80% |
| Phosphate Ester of an Ethoxylated Alcohol having an alkyl group of C$_{8-18}$ and 2-6 moles of ethoxylation per mole of alcohol | 20.00% | 10.00% |
| Emery 622 (coconut fatty acid commercially available from Emery Chemicals) | 0.20% | 0.20% |
| Iodine Premix | 6.50% | 6.50% |
| | 100.00% | 100.00% |

BACTERIOCIDAL EFFICACY

To illustrate typical bacteriocidal efficacy, Working Example 26 was formulated and then tested against a NaOCl control.

| Working Example 26 | |
|---|---|
| Constituent | wt-% |
| Phosphoric Acid (85% w/v) | 34.5 |
| Urea | 47.8 |
| Pluronic P-105 (polyoxyethylene, polyoxypropylene block polymer commercially available from BASF - Wyandotte generally having 76 moles of ethylene oxide and 54 moles of propylene oxide) | 10.0 |
| Emery 622 (coconut fatty acid commercially available from Emery Chemicals) | 0.20 |
| Iodine Premix | 7.50 |

Available Chlorine Germicidal Equivalent Concentration-Official Final Action §§4.012-4.014 A.O.A.C. Methods of Analysis, 14th edition, 1984. The test medium used for product neutralization and survivor growth was Fluid Thioglycollate Medium, Difco Laboratories, Detroit, MI. Salmonella typhi, (ATCC 6539), bacteria were propagated as specified in A.O.A.C. §4.012(d). Prior to exposure the bacteria was incubated for 48 hours at 37° C. The results are reported below with negative signs indicating kill of bacteria over the measured time period.

| RESULTS | | | |
|---|---|---|---|
| Test Date | SAMPLE | ppm | Subculture Series |
| 1/14/88 | NaOCl | 50.0 | - - - - + + + + + + |
| | | 100.0 | - - - - - - + + + + |
| | | 200.0 | - - - - - - - - - - |
| | Example 26 | 25.0 | - - - - - - - - - - |
| 1/19/88 | NaOCl | 50.0 | - - - - + + + + + + |
| | | 100.0 | - - - - - - + + + + |
| | | 200.0 | - - - - - - - - - + |
| | Example 26 | 12.5 | - - - - - - + + + + |
| 1/26/88 | NaOCl | 50.0 | - - - - + + + + + + |
| | | 100.0 | - - - - - + + + + + |
| | | 200.0 | - - - - - - - + + + |
| | | 12.5 | - - - - - + + + + + |
| 3/3/88 | NaOCl | 50.0 | - - - - + + + + + + |
| | | 100.0 | - - - - - - + + + + + |
| | | 200.0 | - - - - - - - - + + + |
| | Example 26 (Trial 1) | 12.5 | - - - - - - + + + + |
| | | 25.0 | - - - - - - - - - - |
| | Example 26 (Trial 2) | 12.5 | - - - - - - + + + + |
| | | 25.0 | - - - - - - - - - - |
| 3/8/88 | NaOCl | 100.0 | - - - - - - + + + + |
| | | 200.0 | - - - - - - - - + + |
| | Example 26 (Trial 1) | 12.5 | - - - - - - + + + + |
| | | 25.0 | - - - - - - - - - - |
| | Example 26 (Trial 2) | 12.5 | - - - - - - + + + + |
| | | 25.0 | - - - - - - - - - - |

From the preceding date it is evident that Example 26 representing a use solution derived from the concentrate composition of the present invention provides sanitizing utility. Specifically, formulatory Example 26, when diluted to 12.5 ppm titratable I$_2$, was equivalent to 100 ppm of available chlorine. Moreover, formulatory Example 26, when diluted to 25.0 ppm titratable I$_2$, was equivalent to 200 ppm available chlorine.

The above discussion, examples and data illustrate our current understanding of the invention. However, since many variations of the invention can be made without departing from the spirit and scope of the invention, the invention resides wholly in the claims hereinafter appended.

I claim as my invention:

1. A storage stable cast solid iodine concentrate composition consisting essentially of:
   (a) an iodine complex consisting essentially of from about 5 wt-% to 25 wt-% of a nonionic surfactant complexing agent and an iodine source present in a ratio of from about 1.5:1 to about 3:1 complexing agent to iodine wherein the concentration of titratable iodine is about 2 wt-% or greater of the composition;
   (b) from about 30 wt-% to 70 wt-% of urea; and
   (c) an effective pH lowering amount of acidulant.

2. The composition of claim 1 wherein said iodine source is an iodine premix composition generally comprising iodine and an iodide salt or iodide acid.

3. The composition of claim 2 wherein said iodide slat is selected from the group consisting of sodium iodide, potassium iodide and mixtures thereof.

4. The composition of claim 2 wherein said iodine acid comprises hydroiodic acid.

5. The composition of claim 1 wherein said nonionic surfactant comprises alkylene oxide moieties selected from the group consisting of polyethylene oxide moieties, polypropylene oxide moieties, or mixtures thereof.

6. The composition of claim 5 wherein said nonionic surfactant is selected from the group consisting of alcohol alkoxylates, or alkyl phenol alkoxylates.

7. The composition of claim 6 wherein said nonionic surfactant has an alkyl moiety ranging in length from about $C_6$ to about $C_{12}$.

8. The composition of claim 5 wherein said nonionic surfactant is selected from the group consisting of $C_{6-12}$ alkyl phenol ethoxylates, and polyoxypropylene/polyoxyethylene copolymers.

9. The composition of claim 8 wherein the nonionic surfactant comprises a nonyl phenol ethoxylate having from about 6 moles to 100 moles of ethoxylation.

10. The composition of claim 8 wherein the nonionic surfactant comprises a polyoxypropylene/polyoxyethylene block copolymer having from about 1 mole to 150 moles to propylene oxide and from about 1 mole to 300 moles of ethylene oxide.

11. A storage stable cast solid iodine concentrate composition consisting essentially of:
   (a) an iodine complex consisting essentially of an iodine source and a complexing agent, said complexing agent consisting of from about 5 wt-% to 25 wt-% of a nonionic surfactant wherein said complexing agent and said iodine are present in a concentration ratio ranging from about 1.5:1 to about 3:1 complexing agent to iodine wherein the concentration of titratable iodine is about 3 wt-% or greater of the composition;
   (b) from about 40 wt-% to 60 wt-% of urea; and
   (c) from about 5 wt-% to 50 wt-% of an acidulant said acidulant selected from the group consisting of phosphoric acid, sodium bisulfate, sulfamic acid, or citric acid.

12. The composition of claim 11 wherein said acidulant is present in a concentration ranging from about 20 wt-% to about 50 wt-%.

13. The composition of claim 11 additionally comprising a defoamer selected from the group consisting of fatty acids, fatty alcohols, and phosphate esters.

14. A use solution resulting from the dilution of the concentrate composition of claim 11 in a diluent to an active iodine concentration of at least 12.5 ppm iodine.

15. An iodine wash concentrate comprising:
   (a) an open face concentrate container; and
   (b) the iodine composition of claim 11 housed in said concentrate container.

16. A pelletized concentrate composition generally comprising the iodine composition of claim 11.

17. A storage stable solid iodine concentrate composition consisting essentially of:
   (a) from about 10 wt-% to about 25 wt-% of an iodine complex, said complex consisting essentially of an iodine source and from about 5 wt-% to 25 wt-% complexing agent in a concentration ratio of at least about 1.5:1 to 3:1 complexing agent to iodine, wherein the concentration or titratable iodine is greater than 3 wt-% of the composition, said complexing agent comprising a nonionic surfactant selected from the group consisting of a polyoxypropylene-polyoxyethylene block copolymer, an alkyl alcohol alkoxylate, or mixtures thereof, and said iodine source comprises iodine;
   (b) from about 40 wt-% to about 60 wt-% of urea; and
   (c) from about 30 wt-% to about 40 wt-% of an acidulant said acidulant comprising a compound selected from the group consisting of phosphoric acid, sodium bisulfate, sulfamic acid, citric acid, or combinations thereof.

18. The composition of claim 17 wherein said iodine source is a premix composition generally comprising iodine and an iodide salt or iodide acid.

19. The composition of claim 18 wherein said iodide salt is selected from the group consisting of sodium iodide, potassium iodide, and mixtures thereof.

20. The composition of claim 18 wherein said iodide acid comprises hydroiodic acid.

21. The composition of claim 17 wherein said complexing agent comprises an alkyl phenol ethoxylate having an alkyl moiety ranging in length from about $C_6$ to about $C_{12}$.

22. The composition of claim 21 wherein said alkyl phenol ethoxylate comprises a nonyl phenol ethoxylate having from about 6 moles to 14 moles of ethoxylation.

23. The composition of claim 17 wherein said complexing agent comprises an alcohol alkoxylate.

24. The composition of claim 23 wherein the alcohol alkoxylate comprises a polyoxypropylene/polyoxyethylene block polymer having from about 30 moles to 70 moles of propylene oxide and from about 4 moles to 80 moles of ethylene oxide.

25. The composition of claim 18 additionally comprising a defoamer, wherein said defoamer is selected from the group consisting of fatty acids, fatty alcohols, and phosphate esters.

26. A use solution resulting from the dilution of the concentrate composition of claim 17 in a diluent to an active iodine concentration of at least 12.5 ppm iodine.

27. An iodine wash concentrate comprising:
   (a) a concentrate container; and
   (b) the iodine composition of claim 17 housed in the concentrate container.

28. A pelletized concentrate composition generally comprising the iodine composition of claim 17.

29. A method of using a storage stable cast solid iodine concentrate composition consisting essentially of a complexing composition, wherein said iodine complex consists essentially of an iodine source and from about 5 wt-% to 25 wt-% of a nonionic surfactant complexing agent, from about 30 wt-% to 70 wt-% of a urea solidifier, and an effective pH lowering amount of an acidulant, said method comprising the step of dissolving said concentrate composition to form an antimicrobial solution and applying said solution to the desired surface.

30. The method of claim 29 wherein said use dilutions comprise an active iodine concentration of at least about 12.5 ppm iodine.

31. The method of claim 29 additionally comprising the step of applying said use dilution composition to the intended surface.

32. The method of claim 29 additionally comprising the steps of:
   (a) further diluting said antimicrobial solution; and
   (b) applying said solution to the intended surface.

33. The composition of claim 1 wherein said nonionic surfactant complexing agent comprises a polyoxyethylene/polyoxypropylene block copolymer, said copolymer selected from the group consisting of a copolymer with 76 moles of ethylene oxide and 54 moles of propylene oxide, a copolymer with 62 moles of ethylene oxide and 54 moles of propylene oxide, or mixtures thereof.

34. The composition of claim 11 wherein said nonionic surfactant complexing agent comprises a polyoxyethylene/polyoxypropylene block copolymer, said copolymer selected from the group consisting of a copolymer with 76 moles of ethylene oxide and 54 moles of propylene oxide, a copolymer with 62 moles of ethylene oxide and 54 moles of propylene oxide, or mixtures thereof.

35. The composition of claim 17 wherein said nonionic surfactant complexing agent comprises a polyoxyethylene/polyoxypropylene block copolymer, said copolymer selected from the group consisting of a copolymer with 76 moles of ethylene oxide and 54 moles of propylene oxide, a copolymer with 62 moles of ethylene oxide and 54 moles of propylene oxide, or mixtures thereof.

36. The method of claim 29 wherein said nonionic surfactant complexing agent comprises a polyoxyethylene/polyoxypropylene block copolymer, said copolymer selected from the group consisting of a copolymer with 76 moles of ethylene oxide and 54 moles of propylene oxide, a copolymer with 62 moles of ethylene oxide and 54 moles of propylene oxide, or mixtures thereof.

* * * * *

UNITED STATES PATENT AND TRADEMARK OFFICE
CERTIFICATE OF CORRECTION

PATENT NO. : 5,310,549

DATED : May 10, 1994

INVENTOR(S) : Sandra L. Bull

It is certified that error appears in the above-identified patent and that said Letters Patent is hereby corrected as shown below:

```
Column 13, line 1, (insert as a heading) insert --
Iodine Stability-- before the words "Table 1"

Column 16, line 55, "compri ng" should read --
comprising--
```

Signed and Sealed this

Twenty-third Day of August, 1994

*Attest:*

BRUCE LEHMAN

*Attesting Officer*     *Commissioner of Patents and Trademarks*